(12) United States Patent
Nishiumi et al.

(10) Patent No.: US 9,896,401 B2
(45) Date of Patent: Feb. 20, 2018

(54) METHOD FOR REMOVING CATALYST USED IN REACTION

(71) Applicant: DAIKIN INDUSTRIES, LTD., Osaka (JP)

(72) Inventors: Masami Nishiumi, Osaka (JP); Daisuke Karube, Osaka (JP)

(73) Assignee: DAIKIN INDUSTRIES, LTD., Osaka (JP)

(*) Notice: Subject to any disclaimer, the term of this patent is extended or adjusted under 35 U.S.C. 154(b) by 0 days.

(21) Appl. No.: 15/538,679

(22) PCT Filed: Dec. 2, 2015

(86) PCT No.: PCT/JP2015/083892
§ 371 (c)(1),
(2) Date: Jun. 22, 2017

(87) PCT Pub. No.: WO2016/104085
PCT Pub. Date: Jun. 30, 2016

(65) Prior Publication Data
US 2017/0349511 A1    Dec. 7, 2017

(30) Foreign Application Priority Data
Dec. 24, 2014   (JP) .................................. 2014-260390

(51) Int. Cl.
*C07C 17/38* (2006.01)
*B01J 38/02* (2006.01)
*B01J 23/26* (2006.01)

(52) U.S. Cl.
CPC ............... *C07C 17/38* (2013.01); *B01J 23/26* (2013.01); *B01J 38/02* (2013.01)

(58) Field of Classification Search
CPC ................................ C07C 17/38; B01J 23/26
USPC ............................................................ 502/56
See application file for complete search history.

(56) References Cited

FOREIGN PATENT DOCUMENTS

| JP | 63-295521 | 12/1988 |
|---|---|---|
| JP | 5-92141 | 4/1993 |
| JP | 10-52642 | 2/1998 |
| JP | 2005-536424 | 12/2005 |
| JP | 2011-529446 | 12/2011 |
| JP | 5915808 | 5/2016 |
| WO | 2010/013796 | 2/2010 |

OTHER PUBLICATIONS

International Search Report issued Feb. 23, 2016 in International (PCT) Application No. PCT/JP2015/083892.
Decision to Grant a Patent issued Mar. 8, 2016 in corresponding Japanese Application No. 2015-235408, with English translation.

*Primary Examiner* — Edward Johnson
(74) *Attorney, Agent, or Firm* — Wenderoth, Lind & Ponack, L.L.P.

(57) ABSTRACT

Provided is a method for easily and safely removing, from a reactor, a catalyst used in a reaction that is performed using hydrogen fluoride in the presence of the catalyst. In a reaction performed in a reactor containing at least hydrogen fluoride and a catalyst, the catalyst is removed through a process comprising a heating step of performing heat-treatment so that the ambient temperature of the reactor is 80° C. or more after completion of the reaction, and a purge step of flowing inert gas into the reactor to discharge the hydrogen fluoride to the outside of the reactor after completion of the reaction.

8 Claims, No Drawings

METHOD FOR REMOVING CATALYST USED IN REACTION

TECHNICAL FIELD

The present invention relates to a method for removing a catalyst from a reactor after a reaction in a reaction system containing hydrogen fluoride, and particularly relates to a method for removing, from a reactor, a catalyst used in the reaction to synthesize fluoroalkanes or fluoroolefins using hydrogen fluoride.

BACKGROUND ART

Catalysts used in chemical reactions mainly have the function of increasing the reaction rate, and are industrially essential materials in the production of desired compounds. Such catalysts are selected depending on the type of each reaction in the synthesis process of chemical products, pharmaceuticals, intermediate raw materials, etc.

For example, fluoroalkanes or fluoroolefins used in heat media, refrigerants, foaming agents, etc., are known to be synthesized by vapor-phase fluorination using hydrogen fluoride, or by dehydrohalogenation. These reactions are generally performed in the presence of a catalyst (for example, see PTL 1). The catalysts used in these reactions are, for example, metal-containing fluoride, chloride, oxide, etc.; however, if such a catalyst is continuously used for a long period of time, the original performance of the catalyst is reduced due to the degradation of the catalyst itself, which may affect the reaction rate, reaction yield, etc. Therefore, regular replacement of the catalyst used in the reaction is generally performed.

As the method for recovering the catalyst used in the reaction when, for example, the reaction system contains toxic gas, such as the hydrogen fluoride mentioned above, the catalyst is removed by, for example, replacing beforehand the inside of the system with inert gas to purge the hydrogen fluoride, and then disassembling the reaction apparatus.

CITATION LIST

Patent Literature

PTL 1: JP2011-529446A

SUMMARY OF INVENTION

Technical Problem

However, even when hydrogen fluoride present in the reaction system was replaced with inert gas, as described above, the hydrogen fluoride remained in some cases. Accordingly, there was a risk of exposing an operator who disassembled the reaction apparatus to hydrogen fluoride, which would be highly dangerous. Moreover, hydrogen fluoride is easily absorbed to catalysts. Accordingly, even when hydrogen fluoride remaining in the reactor was purged with inert gas, there was a risk that hydrogen fluoride absorbed to the removed catalyst would be desorbed later, and that the operator would be exposed to the desorbed hydrogen fluoride. From such a viewpoint, there has been a demand for the construction of a method for easily and safely removing a catalyst used in a reaction containing hydrogen fluoride, after completion of the reaction.

The present invention has been made in consideration of the above circumstances. An object of the present invention is to provide a method for easily and safely removing, from a reactor, a catalyst used in a reaction that is performed using hydrogen fluoride in the presence of the catalyst.

Solution to Problem

The present inventor conducted extensive research to achieve the above object, and consequently found that the above object can be achieved by using a method comprising the steps of, after completion of a reaction performed in the presence of hydrogen fluoride, heating the inside of the reaction system at a predetermined ambient temperature, and purging the inside of the reactor with inert gas. Thus, the present invention has been completed.

More specifically, the present invention relates to the following method for removing a catalyst used in a reaction.

1. A method for removing a catalyst used in a reaction performed in a reactor containing at least hydrogen fluoride and the catalyst, wherein the catalyst is removed through a process comprising:

a heating step of performing heat-treatment so that the ambient temperature of the reactor is 80° C. or more after completion of the reaction; and a purge step of flowing inert gas into the reactor to discharge the hydrogen fluoride to the outside of the reactor after completion of the reaction.

2. The method for removing a catalyst according to item 1, wherein the reaction is vapor-phase fluorination, and a reaction product of the reaction is halogenated hydrocarbon having at least a fluorine group.

3. The method for removing a catalyst according to item 1 or 2, wherein the heat-treatment in the heating step is performed so that $T_2 \geq T_1 - 100$, wherein $T_1$ (° C.) represents the reaction temperature of the reaction, and $T_2$ (° C.) represents the ambient temperature.

4. The method for removing a catalyst according to item 3, wherein heating is performed so that $T_2 \geq T_1$.

5. The method for removing a catalyst according to any one of items 1 to 4, wherein the ambient temperature is 500° C. or less.

6. The method for removing a catalyst according to any one of items 1 to 5, wherein the inert gas has a moisture content of less than 1000 ppm based on the total amount of the inert gas.

7. The method for removing a catalyst according to any one of items 1 to 6, wherein the catalyst is at least one member selected from the group consisting of compounds containing a metal, mixtures containing a metal and activated carbon, and mixtures containing activated carbon and a compound containing a metal.

8. The method for removing a catalyst according to item 7, wherein the metal is at least one member selected from the group consisting of chromium, titanium, aluminum, manganese, nickel, cobalt, iron, copper, zinc, tin, gold, silver, platinum, palladium, ruthenium, rhodium, molybdenum, zirconium, germanium, niobium, tantalum, iridium, hafnium, vanadium, magnesium, lithium, sodium, potassium, calcium, cesium, rubidium, and antimony.

Advantageous Effects of Invention

The method for removing a catalyst according to the present invention can reduce the concentration of hydrogen fluoride remaining in the reactor to a level lower than the conventional level, and particularly remove hydrogen fluoride attached to the catalyst. As a result, the risk that the operator who removes the catalyst from the reaction system is exposed to hydrogen fluoride is reduced. Accordingly, the disassembling of the apparatus used in the reaction, and the removal and replacement of the catalyst used in the reaction can be safely performed.

DESCRIPTION OF EMBODIMENTS

An embodiment of the present invention is described in detail below.

The method for removing a catalyst according to the present invention is characterized in that a catalyst used in a reaction performed in a reactor containing at least hydrogen fluoride and the catalyst is removed after completion of the reaction. Specifically, in the method for removing a catalyst according to the present embodiment, a catalyst used in a reaction containing at least hydrogen fluoride and the catalyst is removed through a process comprising at least the following heating step and purge step.

Heating step: a step of performing heat-treatment so that the ambient temperature of the reactor is 80° C. or more after completion of the reaction.

Purge step: a step of flowing inert gas into the reactor to discharge hydrogen fluoride to the outside of the reactor after completion of the reaction.

The method for removing a catalyst according to the present embodiment can reduce the concentration of hydrogen fluoride remaining in the reactor to a level lower than the conventional level, and particularly remove hydrogen fluoride attached to the catalyst. As a result, the risk that an operator who removes the catalyst from the reactor is exposed to hydrogen fluoride is reduced. Thereby, the disassembling of the apparatus used in the reaction, and the removal and replacement of the catalyst used in the reaction can be safely performed.

The reaction is particularly performed in a reactor containing at least hydrogen fluoride and a catalyst. The reactor further contains materials used as starting materials, optionally added additives, etc.

Hydrogen fluoride may be introduced into the reactor from the reactor inlet. Alternatively, hydrogen fluoride may be introduced by producing it in the reactor by defluorination of a starting material or an intermediate.

The reaction may be performed in a vapor phase or liquid phase, and the reaction form is not particularly limited. In particular, a reaction in a vapor phase, i.e., vapor-phase fluorination, is more suitable for the method for removing a catalyst according to the present embodiment.

The product obtained from the reaction varies depending on the type of starting material used in the reaction. Examples include halogenated hydrocarbon having at least a fluorine group as a substituent. Examples of such halogenated hydrocarbon include alkanes having fluorine and other halogens as substituents, alkenes having fluorine and other halogens as substituents, etc. The type thereof is not particularly limited. The number of carbon atoms of the halogenated hydrocarbon is not particularly limited, and is, for example, 1 to 6, and preferably 1 to 4. Specific examples and preferable examples of the halogenated hydrocarbon are described below.

The halogenated hydrocarbon having a fluorine group is preferably an alkane or alkene having fluorine and other halogens as substituents, that is, an alkane having at least a fluorine group (hereinafter referred to as "fluoroalkane") or an olefin having at least a fluorine group (hereinafter referred to as "fluoroolefin"). Fluoroolefins are compounds that have a carbon-carbon double bond, and have at least fluorine as a substituent. The fluoroalkane or fluoroolefin may have chlorine as a substituent other than a fluorine group.

The fluoroolefin is more preferably propene having at least a fluorine group (i.e., fluoropropene). The fluoropropene may have chlorine as a substituent other than a fluorine group.

More specific examples of the halogenated hydrocarbon having a fluorine group include fluorobutenes, such as 1,1,1,3-tetrafluoro-2-butene (HFO-1354mzf), 2,4,4,4-tetrafluoro-2-butene (HFO-1354mfy), 1,1,1,4,4,4-hexafluoro-2-butene (HFO-1336mzz), 3-trifluoromethyl-4,4,4-trifluoro-1-butene (HFO-1336 mm), 1,1,2,3,3,4,4-heptafluoro-1-butene (HFO-1327pc), and 1,1,1,2,4,4,4-heptafluoro-2-butene (HFO-1327myz); and fluoropropenes or fluoropropynes, such as 2,3,3,3-tetrafluoropropene (HFO-1234yf), 1,3,3,3-tetrafluoropropene (HFO-1234ze), 1,2,3,3-tetrafluoro-1-propene (HFO-1234ye), 3,3,3-trifluoro-1-propene (HFO-1243zf), 1-chloro-3,3,3-trifluoropropene (HCFO-1233zd), 2-chloro-3,3,3-trifluoropropene (HCFO-1233xf), 1,1-dichloro-2,3,3,3-tetrafluoro-1-propene (CFO-1214ya), 1-chloro-2,3,3,3-tetrafluoro-1-propene (HCFO-1224yd), 1,2-dichloro-3,3,3-trichloro-1-propene (HCFO-1223xd), and 3,3,3-trifluoropropyne. Other examples of the halogenated hydrocarbon having a fluorine group include fluoroform (HFC-23), methylene difluoride (HFC-32), fluoromethane (HFC-41), 1,1,1,2,2-pentafluoroethane (HFC-125), 1,1,1,2-tetrafluoroethane (HFC-134a), 1,1,1-trifluoroethane (HFC-143a), 1,1-difluoroethane (HFC-152a), fluoroethane (HFC-161), 1,1,2-trifluoroethylene, 1,1-difluoroethylene, 1-chloro-1,2-difluoroethylene, 2-chloro-1,1,1-trifluoroethane (HCFC-133a), 2-chloro-1,1,1,2-tetrafluoropropane (HCFC-244bb), and the like.

For example, when the reaction product is HFO-1234yf, usable examples of the starting material include 1,1,1,2,2-pentafluoropropane (HFC-245cb), 2,3-dichloro-1,1,1-trifluoropropane (HCFC-243db), 2-chloro-1,1,1,2-tetrafluoropropane (HCFC-244bb), 1,1,1,2,3-pentafluoropropane (HFC-245eb), 1,1,1,2,3-pentachloropropane (HCC-240db), 1,1,2,2,3-pentachloropropane (HCC-240aa), 1-chloro-1,1,2,2-tetrafluoropropane (HCFC-244cc), 1,3,3,3-tetrafluoropropene (HFO-1234ze), 2-chloro-3,3,3-trifluoropropene (HCFO-1233xf), 1,1,3-trichloropropene (HCO-1231ya), 1,1,2,3-tetrachloropropene (HCO-1230xa), and the like.

The type of catalyst is not particularly limited. For example, when the reaction is vapor-phase fluorination mentioned above, and the reaction product is a fluoroolefin mentioned above, a catalyst generally used in this reaction can be used.

Examples of the catalyst include at least one member selected from the group consisting of compounds containing a metal, mixtures containing a metal and activated carbon, and mixtures containing activated carbon and a compound containing a metal.

Examples of the metal include at least one member selected from the group consisting of chromium, titanium, aluminum, manganese, nickel, cobalt, iron, copper, zinc, tin, gold, silver, platinum, palladium, ruthenium, rhodium, molybdenum, zirconium, germanium, niobium, tantalum, iridium, hafnium, vanadium, magnesium, lithium, sodium, potassium, calcium, cesium, rubidium, and antimony.

Examples of compounds containing a metal mentioned above include metal chloride, metal oxide, metal fluoride, metal fluoride chloride, metal oxyfluoride, metal oxychloride, and metal oxyfluoride chloride. When the catalyst is a compound containing a metal, the metal-containing compound may be a catalyst supported on a compound containing one or more different or same metals, which is the so-called carried catalyst. More preferable examples of the metal-containing compound include chromium oxide, alumina, aluminum fluoride, magnesium fluoride, antimony chloride, alumina-supported chromium oxide, zinc-containing chromium oxide, cobalt-containing chromium oxide, aluminum fluoride-supported nickel-containing chromium, and the like.

Examples of mixtures containing a metal and activated carbon include catalysts in which the metal is supported on activated carbon, which are the so-called metal-supported catalysts.

Further, examples of mixtures containing activated carbon and a compound containing a metal include catalysts in which the metal-containing compound is supported on activated carbon, which are the so-called metal compound-supported catalysts. Preferable examples include $Cr_2O_3/C$, $FeCl_3/C$, $SbCl_5/C$, $MgF_2$-containing $Cr/C$, and the like.

These catalysts may be fluorinated.

The temperature of the reaction (hereinafter referred to as the "reaction temperature $T_1$") is not particularly limited. For example, when the product is a fluoroolefin mentioned above, the reaction temperature $T_1$ may be within the range of 80 to 500° C.

The reaction may be performed in a batch manner or a continuous manner; however, in terms of production efficiency etc., the reaction is preferably performed in a continuous manner. Examples of the reaction apparatus include those conventionally used in the reaction of olefins having a fluorine group. Such a reaction apparatus generally comprises a unit of a storage tank for raw materials etc., a reactor for performing a reaction, a distillation column, a storage tank for products, a transport line, and the like. The reaction apparatus can be disassembled. Therefore, when the catalyst is recovered from the reactor after completion of the reaction, the catalyst can be removed from the reactor by disassembling the reaction apparatus.

In general, the inside of the reactor is replaced with inert gas to discharge hydrogen fluoride, which is a toxic gas, before disassembling the reaction apparatus, and the catalyst is then removed. However, in the above reaction, hydrogen fluoride is not only present in the vapor phase of the reactor, but also present in a state of being absorbed to the catalyst. Therefore, when the catalyst is recovered, a conventional method that only replaces the inside of the reaction system with inert gas may make it difficult to safely recover the catalyst by the desorption of hydrogen fluoride attached to the catalyst. Accordingly, in the method for removing a catalyst according to the present embodiment, the catalyst is removed through a process comprising the heating step and purge step mentioned above.

The heating step is to perform heat-treatment so that the ambient temperature of the reactor is 80° C. or more after completion of the reaction.

The heating means is not particularly limited. For example, a heater connected to the reaction apparatus can be used to perform heating so as to obtain a desired ambient temperature.

Heat-treatment in the heating step is performed so that the ambient temperature of the reaction system is 80° C. or more. At an ambient temperature of 80° C. or more, hydrogen fluoride attached to the catalyst is easily desorbed from the catalyst. The ambient temperature after heat-treatment is hereinafter referred to as "$T_2$" (° C.).

It is particularly preferable that heat-treatment in the heating step is performed so that the ambient temperature of the reaction system $T_2 \geq T_1 - 100°$ C. In the formula, $T_1$ represents the reaction temperature $T_1$ mentioned above. That is, it is preferable that the ambient temperature $T_2$ of the reaction system is 100° C. lower than the reaction temperature $T_1$. In this case, hydrogen fluoride attached to the catalyst is more easily desorbed from the catalyst. It is more preferable that heat-treatment in the heating step is performed so that the ambient temperature of the reaction system $T_2 \geq T_1$; that is, heat-treatment is performed so that the ambient temperature is equal to or higher than the reaction temperature.

The upper limit of the ambient temperature of the reaction system is not particularly limited; however, heat-treatment is preferably performed so that the ambient temperature is 500° C. or less. In this case, the time required to remove the catalyst is less likely to be delayed.

The purge step is to flow inert gas into the reactor to discharge the hydrogen fluoride to the outside of the reactor after completion of the reaction. That is, the purge step is to purge hydrogen fluoride with inert gas.

Although the type of inert gas is not particularly limited, nitrogen gas is generally used.

Moreover, the moisture content of the inert gas may be less than 1000 ppm. Due to a moisture content of less than 1000 ppm, the formation of an azeotrope with the raw material used in the reaction can be prevented. The moisture content of the inert gas is preferably 0 ppm or more and less than 10 ppm, more preferably 0 ppm or more and less than 5 ppm, and particularly preferably 0 ppm or more and less than 3 ppm, in terms of capability of preventing the corrosion of the reactor.

When the reaction is performed in a continuous manner, inert gas can be continuously blown into the reactor by flowing in the inert gas from the inlet of the reactor, while flowing out the inert gas from the outlet of the reactor.

The flow rate of inert gas is not particularly limited. For example, when the flow rate of inert gas is 10 mL/min or more per gram of the catalyst placed in the reactor, hydrogen fluoride can be efficiently discharged to the outside of the reactor.

The time of flowing inert gas into the reactor is not particularly limited. For example, when the inert gas is flown for 1 hour or more, the concentration of hydrogen fluoride in the reactor can be sufficiently reduced. In some cases, the inert gas may be continuously flown for 24 hours or more.

The operation of the purge step may be conducted at the same time as the operation of the heating step. Either the purge step or the heating step may be started first. The order of performing these steps is not particularly limited.

More specifically, in the heating step, heat-treatment is performed until the ambient temperature of the reactor reaches a predetermined temperature; however, the operation of the purge step, i.e., purging with inert gas, may be performed during heat-treatment. In this case, purging with inert gas may be started after the ambient temperature reaches a predetermined temperature, or during the increase in the ambient temperature. Further, heat-treatment and purging with inert gas may be performed at the same time by starting purging with inert gas in the purge step, and then performing heat-treatment in the heating step.

After the operations of the heating step and purge step, the catalyst is removed and recovered from the reactor. As described above, the catalyst can be removed from the reactor after disassembling the reaction apparatus. The catalyst may be removed from the reactor through a reactor cleaning step, a cooling step, etc., in addition to the heating step and the purge step.

In the method for removing a catalyst according to the present embodiment, the catalyst is removed through the process comprising the heating step and the purge step; therefore, hydrogen fluoride attached to the catalyst is first desorbed by heat-treatment. The desorbed hydrogen fluoride is then discharged to the outside of the reactor by inert gas. Consequently, the concentration of hydrogen fluoride remaining in the reactor is reduced to a very low level. Accordingly, the risk that when the catalyst is removed from the reactor, an operator who recovers the catalyst is exposed to toxic hydrogen fluoride gas is reduced. Thus, the catalyst can be recovered more safely than before.

EXAMPLES

The present invention is described in detail below with reference to an Example; however, the present invention is not limited to the embodiment of the Example.

Example 1

A chromium oxide catalyst (20.0 g) was placed in a tubular reactor, and the reactor was maintained at atmospheric pressure (0.1 MPa) at 350° C. Anhydrous hydrogen fluoride gas and $CF_3CCl=CH_2$ (HCFO-1233xf) gas were supplied to the reactor, and $CF_3CF=CH_2$ (HFO-1234yf) was synthesized. After completion of the reaction, the ambient temperature of the reactor was changed to 355° C. (heating step), and nitrogen gas with a moisture content of 2.5 ppm was introduced at a flow rate of 200 mL/min (purge step). Then, the concentration of hydrogen fluoride in the reactor after 24 hours was measured. The results confirmed that the concentration of hydrogen fluoride in the reactor was less than 2.5 ppm.

Comparative Example $CF_3CF=CH_2$ (HFO-1234yf) was synthesized under the same conditions as in Example 1. After completion of the reaction, the reactor temperature was changed to 25° C., and nitrogen gas with a moisture content of 2.5 ppm was introduced at a flow rate of 200 mL/min. Then, the concentration of hydrogen fluoride in the reactor after 24 hours was measured. The results confirmed that the concentration of hydrogen fluoride in the reactor was 100 ppm or more, which was an unsafe concentration.

The invention claimed is:

1. A method for removing a catalyst used in a reaction performed in a reactor containing at least hydrogen fluoride and the catalyst, wherein the catalyst is removed through a process comprising:
   a heating step of performing heat-treatment so that the ambient temperature of the reactor is 80° C. or more after completion of the reaction; and
   a purge step of flowing inert gas into the reactor to discharge the hydrogen fluoride to the outside of the reactor after completion of the reaction.

2. The method for removing a catalyst according to claim 1, wherein the reaction is vapor-phase fluorination, and a reaction product of the reaction is halogenated hydrocarbon having at least a fluorine group.

3. The method for removing a catalyst according to claim 1, wherein the heat-treatment in the heating step is performed so that $T_2 \geq T_1 - 100$, wherein $T_1$ (° C.) represents the reaction temperature of the reaction, and $T_2$ (° C.) represents the ambient temperature.

4. The method for removing a catalyst according to claim 3, wherein heating is performed so that $T_2 \geq T_1$.

5. The method for removing a catalyst according to claim 1, wherein the ambient temperature is 500° C. or less.

6. The method for removing a catalyst according to claim 1, wherein the inert gas has a moisture content of less than 1000 ppm based on the total amount of the inert gas.

7. The method for removing a catalyst according to claim 1, wherein the catalyst is at least one member selected from the group consisting of compounds containing a metal, mixtures containing a metal and activated carbon, and mixtures containing activated carbon and a compound containing a metal.

8. The method for removing a catalyst according to claim 7, wherein the metal is at least one member selected from the group consisting of chromium, titanium, aluminum, manganese, nickel, cobalt, iron, copper, zinc, tin, gold, silver, platinum, palladium, ruthenium, rhodium, molybdenum, zirconium, germanium, niobium, tantalum, iridium, hafnium, vanadium, magnesium, lithium, sodium, potassium, calcium, cesium, rubidium, and antimony.

* * * * *